United States Patent [19]

Munib

[11] 4,164,223
[45] Aug. 14, 1979

[54] SURGICAL INSTRUMENT

[76] Inventor: Hamza I. Munib, 131 Liberty St., Petaluma, Calif. 94952

[21] Appl. No.: 821,795

[22] Filed: Aug. 4, 1977

[51] Int. Cl.² ............................................. A61B 17/28
[52] U.S. Cl. ..................... 128/321; 128/346; 417/476; 251/6; 81/425 R; 72/211; 24/115 L
[58] Field of Search .............. 128/321, 322, 346, 325; 417/476; 251/6, 4, 7; 81/425 R, 3 R; 72/211; 24/115 L

[56] References Cited

U.S. PATENT DOCUMENTS

| 1,275,414 | 8/1918 | Forbes | 128/346 |
| 3,194,452 | 7/1965 | Sanderford | 417/476 X |
| 3,407,816 | 10/1968 | Curutchet | 128/321 X |
| 3,648,701 | 3/1972 | Botts | 128/321 |

FOREIGN PATENT DOCUMENTS 278763 10/1951 Switzerland ............................ 128/321

Primary Examiner—Henry J. Recla
Attorney, Agent, or Firm—Flehr, Hohbach, Test, Albritton & Herbert

[57] ABSTRACT

An instrument for use with surgical procedures such as for clearing and disloding the contents of chest tubing, catheters, common duct T-tubing and IV tubing and the like. A pair of rollers are mounted on shafts which are hinged together at one end. A cylindrical handle is mounted on an opposite end of one shaft and an opposed thumb rest is mounted on the end of the other shaft. The hand of a user grasps the handle and thumb rest for moving the rollers into and out of engagement with opposite sides of the tubing. The instrument compresses the tubing and is moved any desired distance along its length for propelling tubing contents or creating suction within the tubing.

1 Claim, 3 Drawing Figures

U.S. Patent
Aug. 14, 1979
4,164,223
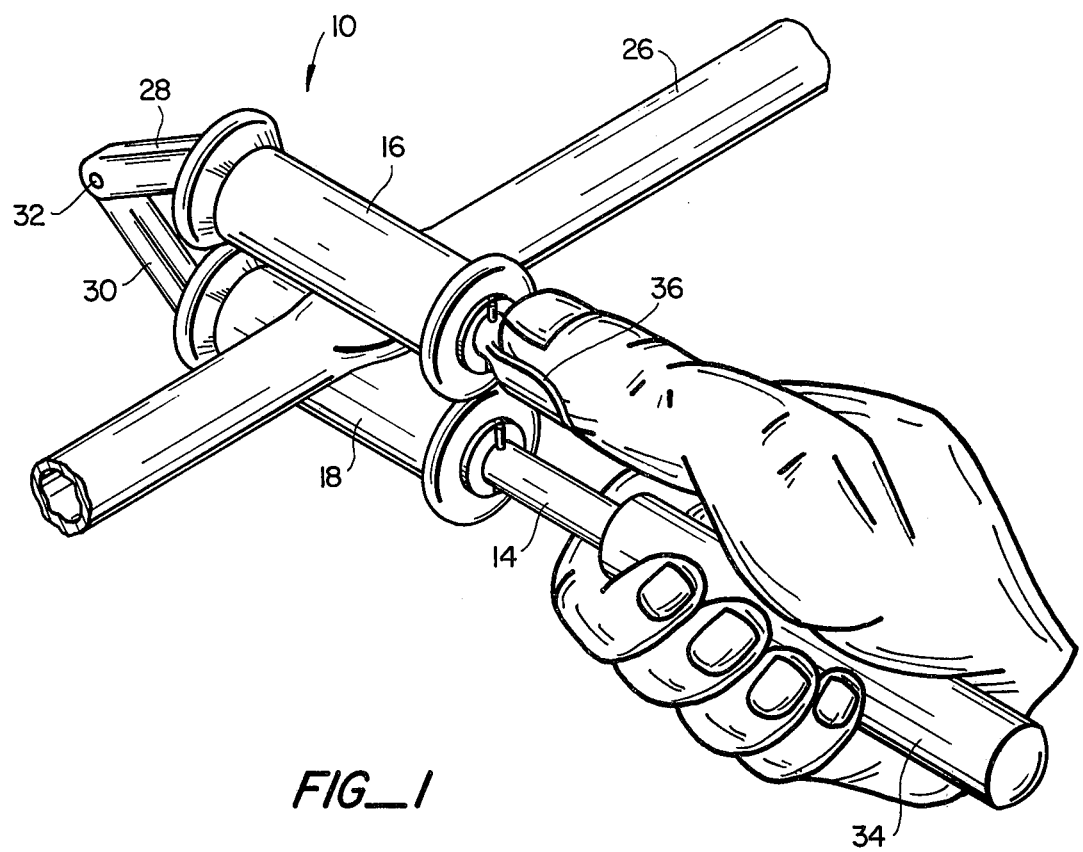
FIG_1
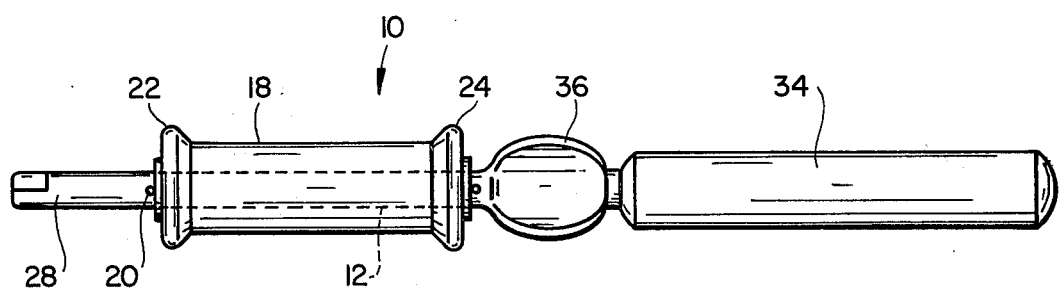
FIG_2
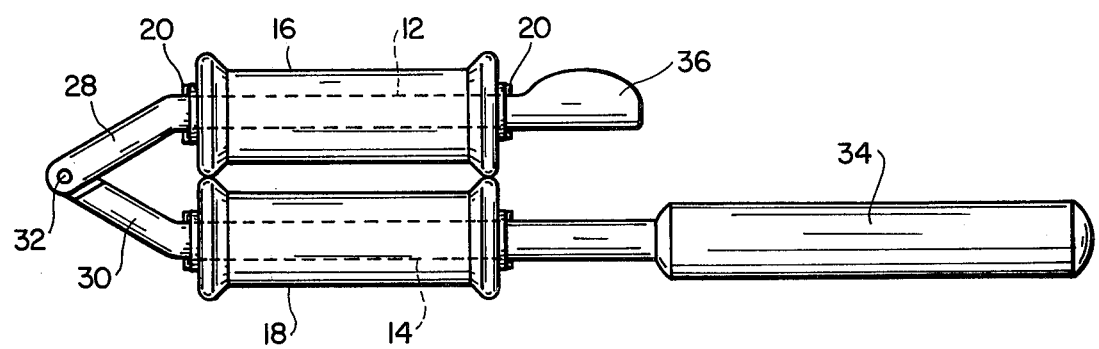
FIG_3

SURGICAL INSTRUMENT

BACKGROUND OF THE INVENTION

This invention relates in general to surgical instruments, and in particular relates to instruments for use with flexible tubing used in surgical procedures.

Heretofore a number of different surgical instruments have been suggested for use with flexible tubing. Among such instruments are those shown in U.S. Pat. Nos. 3,648,701 to Botts, 3,625,472 to Rychlik and 2,245,030 to Gottesfeld. However, such previously suggested instruments have a number of disadvangages and limitations and have not been satisfactory in use and operation.

The surgical instrument suggested by the Botts patent has a number of disadvantages and limitations. The instrument is relatively complicated and would be relatively expensive to manufacture. Different instruments would be required for use by right-handed and left-handed individuals. The instrument could easily become entangled with tubing or fingers, which would be highly objectionable in surgery. When in use the Botts instrument must be employed with a to and fro motion, requiring the operator to be in an awkward position so as to strip the tube by moving the instrument toward him and then toward the patient. The instrument would be difficult to apply because one would have to open the instrument wide to overcome the U-shaped loop or guard before one could place the tubing between the rollers.

The Rychlik patent provides a device having a roller which can variably compress the tube to control the amount of fluid flow, and the Gottesfeld patent provides a roller clamp which is drawn along a tube to move fluid. These patents do not suggest an instrument which would obviate the disadvantages and limitations described above.

OBJECTS AND SUMMARY OF THE INVENTION

It is a general object of the invention to provide a new and improved surgical instrument for use in propelling or clearing the contents of flexible tubing.

Another object is to provide a surgical instrument of the type described which is relatively simple in use and operation; can be easily grasped and applied to the tubing without entanglement; a single instrument can be used by either right-handed or left-handed persons; and can be used in a simple side-to-side mode of operation.

Another object is to provide a surgical instrument of the type described which is simple and inexpensive in construction, can be fabricated from synthetic plastic material, and can be made disposable.

Another object is to provide a surgical instrument of the type described which is more effective and provides advantages when used with chest tubing, catheters, common duct T-tubing and IV tubing.

The invention in summary comprises a pair of shafts upon which rollers are mounted in parallel, spaced-apart relationship. The shafts are hinged together at one end so that the rollers can be pivoted into and out of engagement with opposite sides of tubing. A cylindrical handle extends coaxially from one shaft and a thumb rest extends coaxially from the end of the other shaft. The thumb rest is parallel with and adjacent the handle so that the user's hand can easily grasp the instrument and compress the tubing with the rollers while simultaneously moving the instrument along the tubing with a side-to-side motion for creating suction or propelling contents along the tubing.

The foregoing and additional objects and features of the invention will appear from the following description in which the several embodiments have been set forth in detail in conjunction with the accompanying drawings.

BRIEF DESCRIPTION OF THE DRAWINGS

FIG. 1 is a perspective view of the surgical instrument of the invention shown in use with tubing.

FIG. 2 is a top plan view of the instrument of FIG. 1.

FIG. 3 is a side elevational view of the instrument of FIG. 1.

DESCRIPTION OF THE PREFERRED EMBODIMENTS

The drawings illustrate generally at 10 a surgical instrument made in accordance with the invention. The instrument 10 includes the pair of shafts 12,14 upon which rollers 16,18 are respectively mounted for rotation. Fastener pins 20 are provided at opposite ends of the rollers to hold the latter in place on the shafts in parallel, spaced-apart relationship. The rollers are formed with end flanges 22,24 to assist in guiding the instrument along the tubing 26 when in use.

Common ends of the shafts are formed with bight portions 28,30 which are coupled together by hinge pin 32 to permit the shafts to pivot in a scissors-like action. The opposite end of the shaft 14 supports an elongate cylindrical handle 34 which is sized to comfortably fit in the palm of the user's hand. The corresponding end of shaft 12 carries a cup-shaped thumb support 36. The thumb support and handle extend coaxially of the respective shafts and are positioned in parallel, spaced-apart relationship so that either the left or right hand of a user can comfortably grasp the instrument in the manner shown in FIG. 1.

The use and operation of the invention is as follows. With the rollers pivoted apart the tubing can be easily inserted without entanglement between the rollers. One hand is then employed to grasp the instrument as shown in FIG. 1 and apply pressure between the handle and thumb support so that the rollers are brought into engagement with and compress the tubing. With a side-to-side action the instrument can be rolled along the length of the tubing while compressed for propelling tubing contents or creating suction within the tubing.

The surgical instrument of the invention has application with chest tubing commonly used with most chest and heart operations, for chest trauma, pneumothorax, hemothorax, and spontaneous pneumothorax. Since it is essential that the draining tube remain patent, the tubes must be "milked." This is conventionally done by occluding the tube with the left hand at a point near to the patient, then "milking" the tube toward the collecting drainage bottle or pleur-evac by using the right hand, thus creating a negative pressure zone at the "milked" segment of the tube. The left hand is then let go to effect a mild suction effect at a portion of the tube inside the patient's chest cavity. This is very effective in dislodging and suctioning a fibrin plug or clot (should one exist). The surgical instrument of the present invention when used in the manner described accomplishes this object more effectively and efficiently because it saves wear on the hand of the user, and it does not cause snap-back action of the tube when the left hand is released which could dislodge the entire tube from the patient's chest and thereby create a severe problem. The use of the present invention can also create a small, moderate or large degree of suction effect as desired by rolling the instrument over a short, medium or longer length of the tube. The surgical instrument also fits any size of tubing up to 2.5 cm width (when compressed).

The surgical instrument of the invention also has application with catheters. A bladder catheter is used anytime a retention catheter is needed, is used for open prostatectomies, and for transurethral resections. Because it is essential that the catheter remain patent, the catheter must be irrigated under strict sterile techniques. If infection occurs because of a break in this technique, it could be troublesome. Use of the surgical instrument of the present invention in the manner described can, for catheters, lessen the frequency of irrigation and in certain cases eliminate the need for it completely. No sterile technique is required, thus decreasing the exposure to infection. Use of the instrument also does not cause rupture of the indwelling balloon.

The surgical instrument of the invention is also used in the manner described for common duct T-tubing. If a common duct T-tube stops draining then the possibility of "gravel," "concretion" and the like blocking the T-tube intraductal openings exist. The present invention can be used to suction out the blocking material and has the advantage of avoiding irrigation which must be done under strict sterile technique and which otherwise would result in the possibility of pushing the blocking material toward the common-duct and risk obstruction of the ampulla.

The invention further has application for IV tubing. It is important that the IV runs into the vein especially if the IV contains substances that are not to be injected subcutaneously. To assure this, it is necessary to either (a) disconnect the IV tubing from the needle or the plastic IV cath, which may lead to contamination and spillage of blood on the patient's bedding, or (b) the IV bottle must be lowered below the level of the patient in order to effect a siphoning action and detect return of blood into the tubing, which is a time consuming and cumbersome procedure. Moreover, both procedures (a) and (b) are typically not done frequently enough. The surgical instrument of the present invention, because of its simplicity, will more frequently be used so that venous return can be detected and thereby achieve the desired therapeutic effect of the IV fluid and medications as well as eliminate subcutaneous extravasation of irritating materials.

While the foregoing embodiments are at present considered to be preferred it is understood that numerous variations and modifications may be made therein by those skilled in the art and it is intended to cover in the appendant claims all such variations and modifications as followed within the true spirit and scope of the invention.

What is claimed:

1. A surgical instrument for use with resilient tubing such as chest tubing, catheters, common duct T-tubing and IV tubing, comprising the combination of a pair of parallel elongated shafts each having first and second ends, said first ends of said shafts being pivotally mounted together for pivotal movement about an axis, a pair of cylindrical rollers mounted for rotation on each shaft, respectively and lying in a plane perpendicular to said pivot axis, said rollers being oriented in parallel, spaced-apart relationship for movement into and out of engagement with opposite sides of the tubing, an elongate first handle mounted on and extending coaxially from a second end of said shafts and the rollers in a direction remote from the hinge, and a thumb rest mounted on and extending coaxially from a second end of the other shaft and roller, said thumb rest being disposed in spaced relationship with the handle whereby the user's hand can simultaneously grasp the handle and thumb rest for moving the rollers at right angles to and against the tubing while also moving the rollers along the length of the tubing.

* * * * *